(12) United States Patent
Krishnamachari (10) Patent No.: US 6,453,191 B2
(45) Date of Patent: Sep. 17, 2002

(54) AUTOMATED INTERPRETATION OF T-WAVE ALTERNANS RESULTS

(75) Inventor: Srivathsan Krishnamachari, Cambridge, MA (US)

(73) Assignee: Cambridge Heart, Inc., Bedford, MA (US)

( * ) Notice: Subject to any disclaimer, the term of this patent is extended or adjusted under 35 U.S.C. 154(b) by 0 days.

(21) Appl. No.: 09/785,558

(22) Filed: Feb. 20, 2001

Related U.S. Application Data

(60) Provisional application No. 60/183,335, filed on Feb. 18, 2000.

(51) Int. Cl.[7] ............................................. A61B 5/0452
(52) U.S. Cl. ..................................................... 600/515
(58) Field of Search ................................. 600/515, 516, 600/517, 518, 519, 509

(56) References Cited

U.S. PATENT DOCUMENTS

| 4,802,491 A | 2/1989 | Cohen et al. |
| 5,265,617 A | 11/1993 | Verrier et al. |
| 5,935,082 A | 8/1999 | Albrecht et al. |

*Primary Examiner*—Scott M. Getzow
(74) *Attorney, Agent, or Firm*—Fish & Richardson P.C.

(57) ABSTRACT

Interpreting alternans data includes accessing alternans data and automatically evaluating the alternans data to produce one or more interpretation parameters based on the alternans data. The interpretation parameters are used to generate interpretation results related to the alternans data. Finally the interpretation results are made accessible for examination.

67 Claims, 9 Drawing Sheets

| Electrode Name | Electrode Location | Type | Available Signals |
|---|---|---|---|
| RL | R. ILLIAC CREST | STANDARD | (DRIVEN GROUND) |
| RA | RIGHT SHOULDER | STANDARD | (REFERENCE) |
| LA | L. SHOULDER | STANDARD | LA |
| LL(F) | L. ILLIAC CREST | MULTIPLE | LLa, LLb, LLc, LLi |
| V1 | V1 | STANDARD | V1 |
| V2 | V2 | MULTIPLE | V2, V2a, V2i |
| V3 | V3 | STANDARD | V3 |
| V4(C) | V4 | MULTIPLE | V4, V4a, V4i |
| V5 | V5 | STANDARD | V5, V5a, V5i |
| V6(A) | V6 | MULTIPLE | V6, V6a, V6b, V6i |
| I | R. V6 POSITION | MULTIPLE | I, Ia, Ib, Ii |
| H | BELOW NECK | MULTIPLE | H, Ha, Hi |
| E | BETWEEN A & I | STANDARD | E |
| M | BACK | STANDARD | M |

| Node on Classification Flowchart | Classification | Message |
|---|---|---|
| A | Positive | Sustained alternans at rest, consistent with positive tracing |
| B | Positive | Sustained alternans with onset <=[Pos HRT] BPM, consistent with positive tracing |
| C | Indeterminant | Sustained alternans with onset > [Pos HRT] BPM and maximum negative HR < [Neg HRT] BPM, consistent with indeterminant tracing |
| D | Negative | Sustained alternans with onset > [Pos HRT] BPM and maximum negative HR [Neg HRT] BPM, consistent with negative tracing |
| E | Indeterminant | No sustained alternans, maximum negative HR < [Neg HRT] BPM and maximum HR < [Max HRT] BPM, consistent with indeterminant tracing |
| F | Indeterminant | No sustained alternans, maximum negative HR < [Neg HRT] BPM and maximum HR[Max HRT] BPM, consistent with indeterminant tracing |
| G | Negative | No sustained alternans, maximum negative HR < [Neg HRT] BPM, maximum HR[Max HRT] BPM, and maximum negative HR close to maximum HR, consistent with negative tracing |
| H | Negative | No sustained alternans and maximum negative HR [Neg HRT] BPM, consistent with negative tracing |

9005

AUTOMATED INTERPRETATION OF T-WAVE ALTERNANS RESULTS

This application claims priority from U.S. Provisional Application No. 60/183,335, titled "Automated Interpretation of T-Wave Alternans Results" and filed Feb. 18, 2000, which is incorporated by reference in its entirety.

TECHNICAL FIELD

The invention is directed to interpretation of alternans results derived from an electrocardiogram (ECG) waveform.

BACKGROUND

Alternans, a subtle beat-to-beat change in the repeating pattern of an (ECG) waveform can be indicative of electrical instability of the heart and increased susceptibility to sudden cardiac death. Alternans results in an ABABAB . . . pattern of variation of waveform shape between successive beats in an ECG waveform. The level of variation has been found to be a useful characterization of an individual's cardiac electrical stability, with increasing variation being indicative of decreasing stability.

While an ECG waveform typically has an amplitude measured in millivolts, an alternans pattern of variation with an amplitude on the order of a microvolt may be clinically significant. Accordingly, the alternans pattern may be too small to be detected by visual inspection of the electrocardiogram and often must be detected and quantified electronically. Such electronic detection and quantification of the alternans pattern is further complicated by the presence of noise in the ECG waveforms, as the noise may result in beat-to-beat variations that have a larger magnitude than the alternans pattern of variation.

Also, noise in the ECG waveform can mimic the presence of alternans where none exists. For example, if a patient is breathing at one half of the heart rate, the respiration may introduce a harmonic signal having the ABABAB . . . pattern of alternans. Motion that repeats with some periodicity, such as that resulting from exercise, can create noise with a similar pattern.

There are several known methods for measuring the level of alternans present in an electrocardiogram (ECG). Examples include the methods described in U.S. Pat. Nos. 4,802,491 and 5,265,617, which are incorporated by reference. Devices measuring alternans may print an alternans trend report showing the level of alternans in the individual ECG leads for the duration of the ECG recording, along with other reference signals such as measures of heart rate, noise, abnormal beats, and artifacts. An example of an alternans trend report is described in U.S. Pat. No. 5,935,082, which are incorporated by reference.

SUMMARY

In one general aspect, interpreting alternans data includes accessing alternans data and automatically evaluating the alternans data to produce one or more interpretation parameters based on the alternans data. The interpretation parameters are used to generate interpretation results related to the alternans data. Finally, the interpretation results are made accessible for examination.

Implementations may include one or more of the following features. For example, accessing the alternans data may include receiving the alternans data from an electrocardiogram system or reading stored alternans data from a storage medium. Accessing the alternans data also may include calculating the alternans data from electrocardiogram data.

The alternans data may include alternans measures and also may include a reference signal associated with a factor that affects the quality of the alternans measures or the generation of the alternans. For example, with respect to the quality of the alternans measures, the reference signal may include a signal that masks or mimics the presence of alternans. The reference signal also may include a measure of noise that exists in the alternans data. Signals that may affect the generation of alternans include, for example, a measure of the patient's heart rate or respiratory activity.

The interpretation parameters may include a measure of a highest heart rate in the alternans data or a highest heart rate at which sustained alternans is definitely not present. Other examples include a measure of a heart rate above which sustained alternans exists and below which sustained alternans does not exist, or an indication of the existence or nonexistence of sustained alternans.

Automatically evaluating the alternans data may include automatically evaluating a measure of alternans that is indicative of the presence of sustained alternans. For example, the measure of alternans may include a measure of a voltage or of an area associated with the alternans. Likewise, the measure of the alternans may include a measure of a power spectrum of the alternans or a dynamically estimated magnitude of the alternans, obtained, for example, by complex demodulation of the electrocardiogram. A measure of noise associated with the alternans, e.g., a measure of a standard deviation of the noise, also may be indicative of sustained alternans. Other examples include measures of a temporal duration of the alternans, of gaps in the alternans, or of a measure of the alternans based upon evaluation of time reversed alternans data.

Automatically evaluating the alternans data may include, for example, automatically using a first search to search the alternans data for sustained alternans. After using the first search, a different search also may be used to search the alternans data for sustained alternans. The different search may be used, for example, when the first search does not find sustained alternans in the alternans data or when a determination is made that the findings of the first search are suspect as a result of a poor quality of the alternans data.

Automatically evaluating the alternans data also may include evaluating the data provided by an individual electrocardiogram lead or evaluating a combination of adjacent precordial electrocardiogram leads.

The interpretation results that are generated may include the interpretation parameter and/or a clinical interpretation regarding the existence of sustained alternans in the alternans data. The clinical interpretation may, for example, positively indicate the existence of sustained alternans, negatively indicate the existence of sustained alternans, or indicate that the existence of sustained alternans is indeterminate.

Using the interpretation parameter to calculate the interpretation results may include using the interpretation parameter to traverse a decision tree to produce the interpretation results based on the alternans data. Another example includes comparing the interpretation parameter to a heart rate threshold to produce the interpretation results based on the alternans data.

The interpretation results may be made accessible for examination by, for example, graphically displaying the alternans measure, the reference signal, and the interpretation results. The interpretation results also may be made accessible by storing the alternans measure, the reference signal, and/or the interpretation results in a human or machine readable format. In any event, the alternans measure and the reference signal may be displayed using a common time axis and the interpretation results may be graphically associated to an associated feature of the alternans measure and/or the reference signal. A message describing the interpretation results also may be included.

The alternans trend report is evaluated by a trained physician, who assigns a clinical interpretation of "positive," "negative" or "indeterminate" to the alternans result. The alternans trend data may be difficult to interpret, especially when the alternans exists in the presence of noise or abnormal ECG beats. Ultimately, the physician must exercise subjective judgment based on his or her own experience and training to determine whether the alternans is significant and sustained, and to estimate the values of Onset HR (the heart rate at the onset of sustained alternans), Max Neg. HR (the highest heart rate at which alternans is definitively not present), and other parameters. The accuracy and reliability of the interpretation of the trend data therefore varies from physician to physician as a function of experience and training. This inter-reader variability diminishes the predictive value of the alternans test and is avoided by the automatic interpretation.

These general and specific aspects may be implemented using a method, a system, or a computer program, or any combination of system, methods, and computer programs.

Other features and advantages will be apparent from the following description, including the drawings, and from the claims.

DETAILED DESCRIPTION

Figure 1:
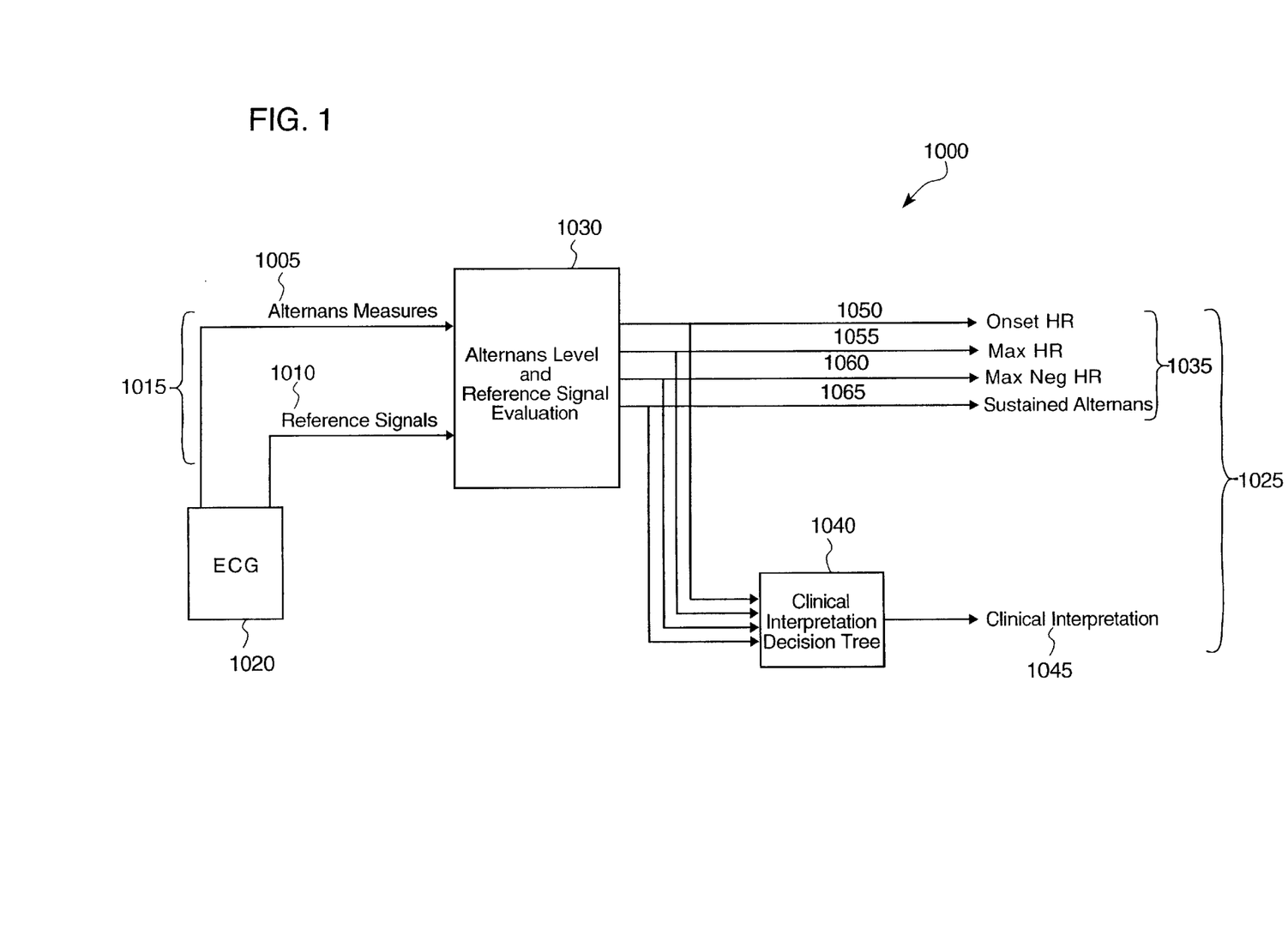
FIG. 1 is a schematic block diagram of an automated system for interpretation of T-wave alternans results.

FIG. 1 illustrates an analysis system 1000 that automatically interprets alternans results. The analysis system 1000 may access and analyze, for example, alternans measures 1005 and other signals 1010 which are referred to together as alternans data 1015. The alternans data 1015 may be provided by an electrocardiogram (ECG) system 1020 that may be included in the system 1000. The system 1000 analyzes the alternans data 1015 to generate interpretation results 1025.

The system 1000 may present the interpretation results 1025 to a physician or other operator of the system 1000 by, for example, displaying them on a monitor (not shown) or by generating a printed representation of them using a printer (not shown).

Figure 2:
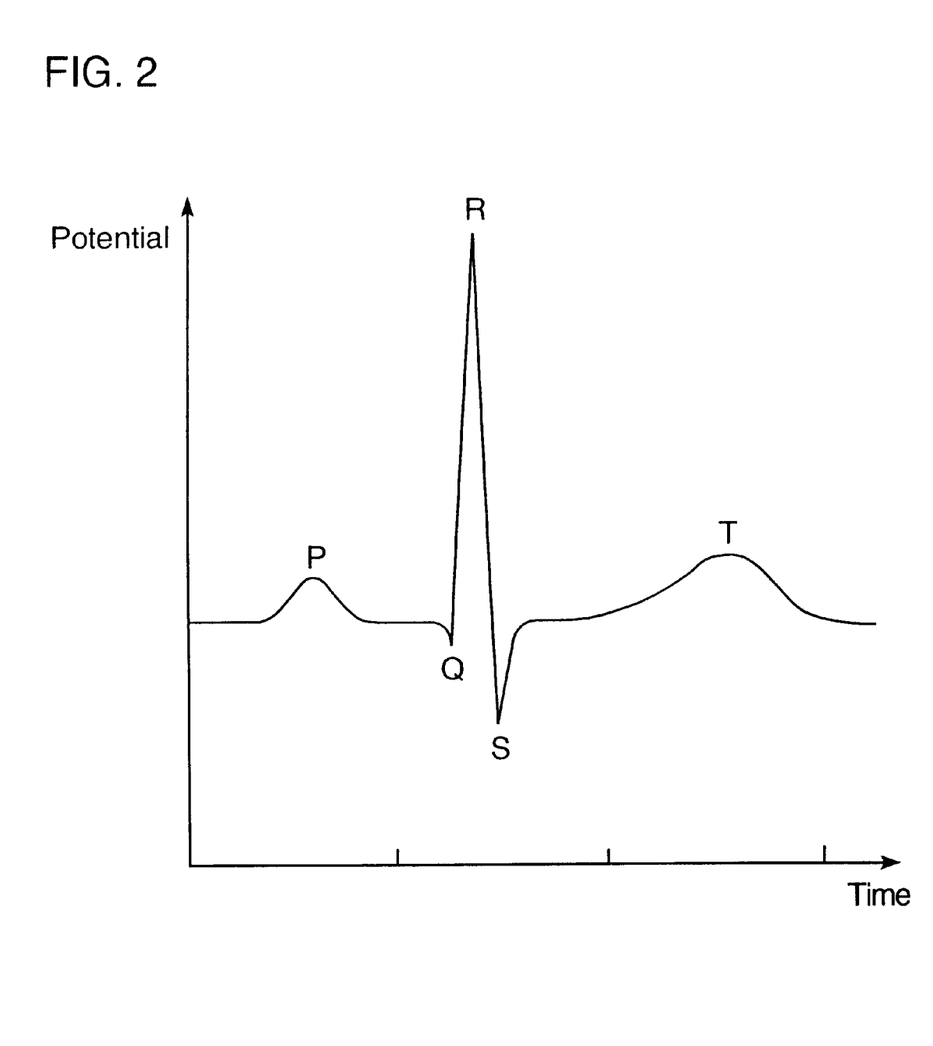
FIG. 2 is a graph of an ECG waveform for a single beat.

Referring to FIG. 2, an ECG waveform for a single beat is typically referred to as a PQRST complex. Briefly, the P wave appears at initiation of the beat and corresponds to activity in the atria, while the QRST complex follows the P wave and corresponds to ventricular activity. The QRS component represents the electrical activation of the ventricles, while the T-wave represents their electrical recovery. The ST segment is a relatively quiescent period. It has been found that the T-wave is the best interval of the ECG complex for detecting alternans. That is, a level of variation in the T-waves of alternating beats is the best indicator of the electrical stability of the ventricles, which are the main pumping chambers of the heart.

For clarity of exposition, it is helpful to discuss the ECG system 1020 and the generation by the ECG system 1020 of the alternans results 1015. A clear understanding of various signals that may be included in the alternans results 1015 is useful in comprehending subsequent analysis by the system 1000 of the alternans results 1015.

An ECG signal measured at a body surface may be represented by modeling the heart as a three-dimensional dipole source that produces an electrical signal that varies based on the distance from the heart in the X, Y and Z directions. Thus, the voltage detected by an electrode M that is located relative to the dipole at a coordinate given by the vector (xM,yM,zM) will be:

$$M(t)=xMvX(t)+yMvY(t)+zMvZ(t).$$

Use of the dipole vector model of the heart has lead to the development of clinical systems that measure the X, Y and Z components of the dipole source through a linear combination of several electrodes. The most common known XYZ systems are the Frank lead system and the Bipolar system. In clinical practice, another common system of electrodes is the twelve lead system. The twelve lead system places greater emphasis on the electrodes on the left chest near the heart.

Figure 3:
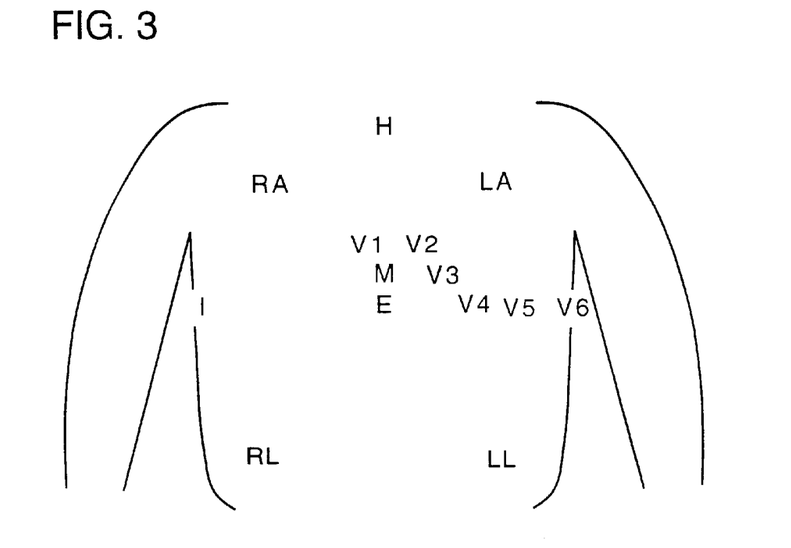
FIG. 3 is a placement diagram for the placement of ECG electrodes on a patient.
Figure 4:
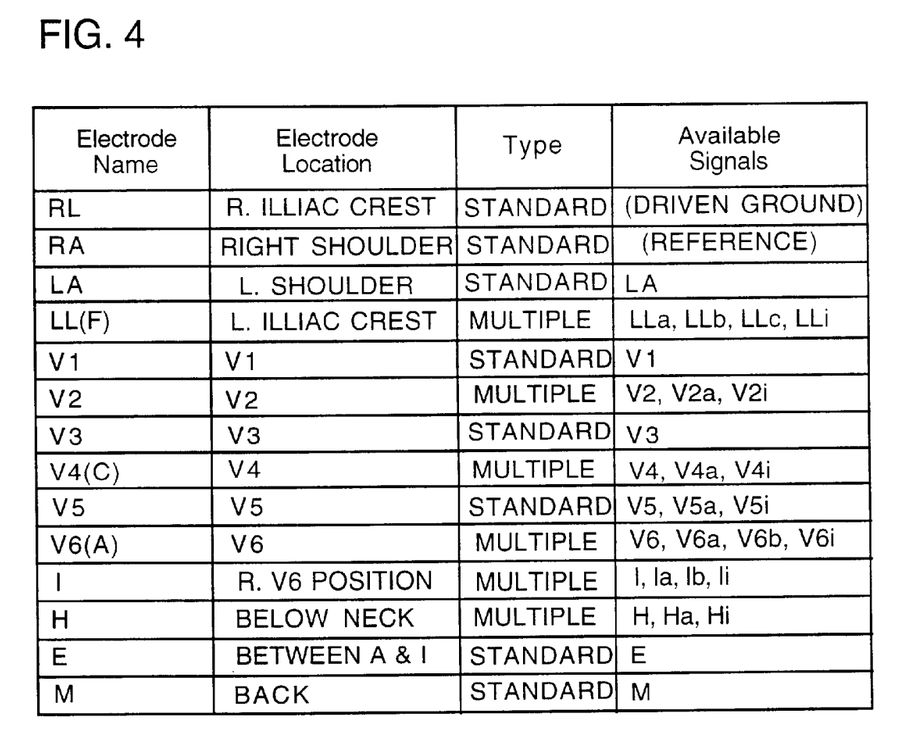
FIG. 4 is a table illustrating the location and type of the electrodes of FIG. 3 and defining the input signals that are recorded from those electrodes.

The ECG system 1020 may include fourteen electrodes that are placed on the patient as illustrated in FIG. 3. This arrangement combines the electrodes of the Frank and standard 12 lead systems. The signals produced by the electrodes, along with their types, are illustrated in FIG. 4. Seven of the electrodes are conventional ECG electrodes having a single terminal (and producing a single signal), while the other seven electrodes are multi-segment electrodes having four terminals (and producing up to four signals).

The ECG system 1020 may periodically sample the signals. When recording a signal, the ECG system 1020 uses an isoelectric point of the signal as a zero voltage reference. The ECG system 1020 measures the isoelectric point during the PQ interval between the P wave and QRS complex. The PQ interval is a good approximation to a zero ECG level because there is no major electrical activity in the heart at that time.

After acquiring the signals, the ECG system 1020 processes the signals to produce an ECG waveform for further analysis or display. While an ECG waveform typically has a QRS amplitude measured in millivolts, an alternans pattern of variation with an amplitude on the order of a microvolt may be clinically significant. Accordingly, the ECG system 1020 must produce the ECG waveform with extreme accuracy to permit effective detection of alternans. Achievement of this accuracy is complicated by the presence of noise in the electrode signals. The noise may result in beat-to-beat variations in the ECG waveform that have a larger magnitude than the alternans pattern of variation.

Noise in the ECG waveform can mask the presence of alternans. The noise also can mimic the presence of alternans where there is none. For example, if a patient is breathing at one-half of the heart rate, the respiration may introduce a harmonic signal having the ABABAB... pattern of alternans. In addition, motion that repeats with some periodicity, such as that resulting from exercise, can create noise with a similar pattern. Furthermore, noise resulting from different sources, such as respiration and electrode noise, can interact and produce new periodicities, one of which may mimic or mask alternans.

The ECG system 1020 may be configured to reduce the noise in the ECG waveforms before producing measures of alternans. For example, the ECG system 1020 may combine one or more ECG signals and one or more other signals in a way that causes the noise content of the signals to combine destructively while preserving the ECG content.

The ECG system 1020 may obtain thirty-two signals from the fourteen leads illustrated in FIG. 3. These thirty-two signals may be used by the ECG system 1020 to produce a set of low-noise ECG signals (e.g., V1, V2, V3, V4, V5, and V6). The ECG system 1020 then may use the set of low-noise ECG signals to produce low noise vector signals (VM, X, Y, Z) using, for example, a vector enhancement technique. In some instances, the ECG system 1020 may produce other combinations of low-noise ECG signals. The ECG system 1020 also may associate a high noise flag with the ECG signals. The ECG System 1020 may set the high noise flag if noise in the vector magnitude ECG lead VM is greater than HIGH_NOISE_THRESHOLD, a value of about 1.8 $\mu$V, and if the noise level plus the alternans level in VM is greater than NOISE_ALT_THRESHOLD, a value of about 2.5 $\mu$V.

The ECG system 1020 then may generate alternans measures 1005 based on the low-noise ECG signals. For example, the ECG system 1020 may generate alternans measures 1005 through power spectrum (Fourier) analysis of the signals. Alternatively, time domain analysis may be employed, such as, for example, complex demodulation, estimation by subtraction, least squares estimation, autoregressive estimation, and/or auto-regressive moving average estimation.

The ECG system 1020 also may generate measures of a group of reference signals 1010 that represent factors that may affect the quality of the alternans measures 1005. The reference signals 1010 may include measures of the heart rate, the relative number of bad or abnormal beats, the noise level, the exercise rate (when exercise is used to stimulate the heart), the respiratory activity, and variations in the heart rate. The reference signals 1010 may be generated by the ECG system 1020 using techniques similar to those employed in generating alternans measures 1005.

Using the generated measures of the alternans 1005 and other reference signals 1010, the ECG system 1020 may generate a T-wave alternans trend report showing the level of T-wave alternans in the individual ECG leads for the duration of the ECG recording, along with other reference signals such as measures of heart rate, noise, abnormal beats, and artifacts. An example of a T-wave alternans trend report is described in the incorporated U.S. Pat. No. 5,935,082, hereinafter incorporated by reference in its entirety.

Referring back to FIG. 1, the system 1000 includes an evaluation system 1030 configured to access and evaluate the alternans results 1015 and to produce interpretation parameters 1035 based on the alternans results 1015. The system 1000 also includes an interpretation system 1040 configured to access the interpretation parameters 1035 and to produce a clinical interpretation 1045 based on the interpretation parameters 1035.

The evaluation system 1030 takes as its input the alternans measures 1005, such as, for example, alternans levels in the individual ECG leads for points along the time-course of the ECG recording. The evaluation system 1030 also takes reference signals 1010 along the time-course of the recording, such as, for example, ECG noise levels, heart rate, variation in heart rate, respiration, noise level relative to alternans level, and a list of abnormal beats. The evaluation system 1030 applies a set of definitions and rules to the input data (explained in more detail below and with respect to FIG. 5), such as, for example, Onset HR value and time 1050, Max HR value and time 1055, Max Neg. HR value and time 1060, and Sustained Alternans (Present/Absent/Present at Rest) 1065.

Prior to proceeding with the description of the interpretation parameters it is helpful to define a number of fundamental terms that are relied upon in the description of the interpretation parameters.

A smoothed heart rate is a heart rate obtained by applying to a heart rate signal a smoothing function, such as, for example, a low-pass filter.

An interval may be defined as an intervening period of time in a time signal (e.g., a heart rate signal), and the signal may be broken into multiple non-overlapping uniform intervals, such as, for example, intervals of 60 seconds.

A clean interval may be defined as an interval in which there are not significant bad/abnormal beats, noise, or leads-off conditions for at least a time period of MIN_CLEAN_INT of the interval duration (e.g., 50 seconds for a 60 second interval).

An interval heart rate is the lowest of all of the smoothed heart rates in the interval.

A negative interval is a clean interval that does not begin or end with bad beats, noise, or alternans. Additionally, in a negative interval, alternans must account for no more that MAX_NEG_ALT of the interval duration (e.g., 10 seconds for a 60 second interval).

The minimum clean heart rate may be defined as the lowest interval heart rate of all of the clean intervals.

Returning again to the interpretation parameters, the Onset HR 1050 may be determined as a heart rate threshold above which significant alternans is consistently present and below which significant alternans is not consistently present. Where multiple sustained alternans are revealed, the Onset HR 1050 may be selected as the lowest detected heart rate threshold above which significant alternans is consistently present and below which significant alternans is not consistently present. The Onset HR time may be defined as the start time of the onset heart rate interval.

The Max HR 1055 may be determined as the highest of all one-minute interval heart rates in the ECG record. The Max HR time may be determined as the time associated with the midpoint of the one-minute interval with which the Max HR 1055 is associated.

The Max Neg. HR 1060 may be determined by examining all of the negative intervals prior in time to the Onset HR interval. The Max Neg. HR 1060 then may be selected as the highest interval heart rate from among the examined negative intervals. The Max Neg. HR time is defined as the time associated with the midpoint of the one-minute interval to which the Max Neg. HR 1060 is associated. However, if the Max Neg. HR 1060 corresponds to the interval immediately prior to the interval associated with the Onset HR 1050, then the Max Neg. HR 1060 is changed to be equal to the Onset HR 1050 and the Max Neg. HR time is set equal to the Onset HR time.

Sustained alternans may be determined to be "Present," "Absent" or "Present at Rest." A determination of "Present" indicates generally that sustained alternans has been detected while a determination of "Absent" indicates that sustained alternans has not been detected. A determination of "Present at Rest" indicates that sustained alternans has been detected at a resting heart rate.

Figure 5:
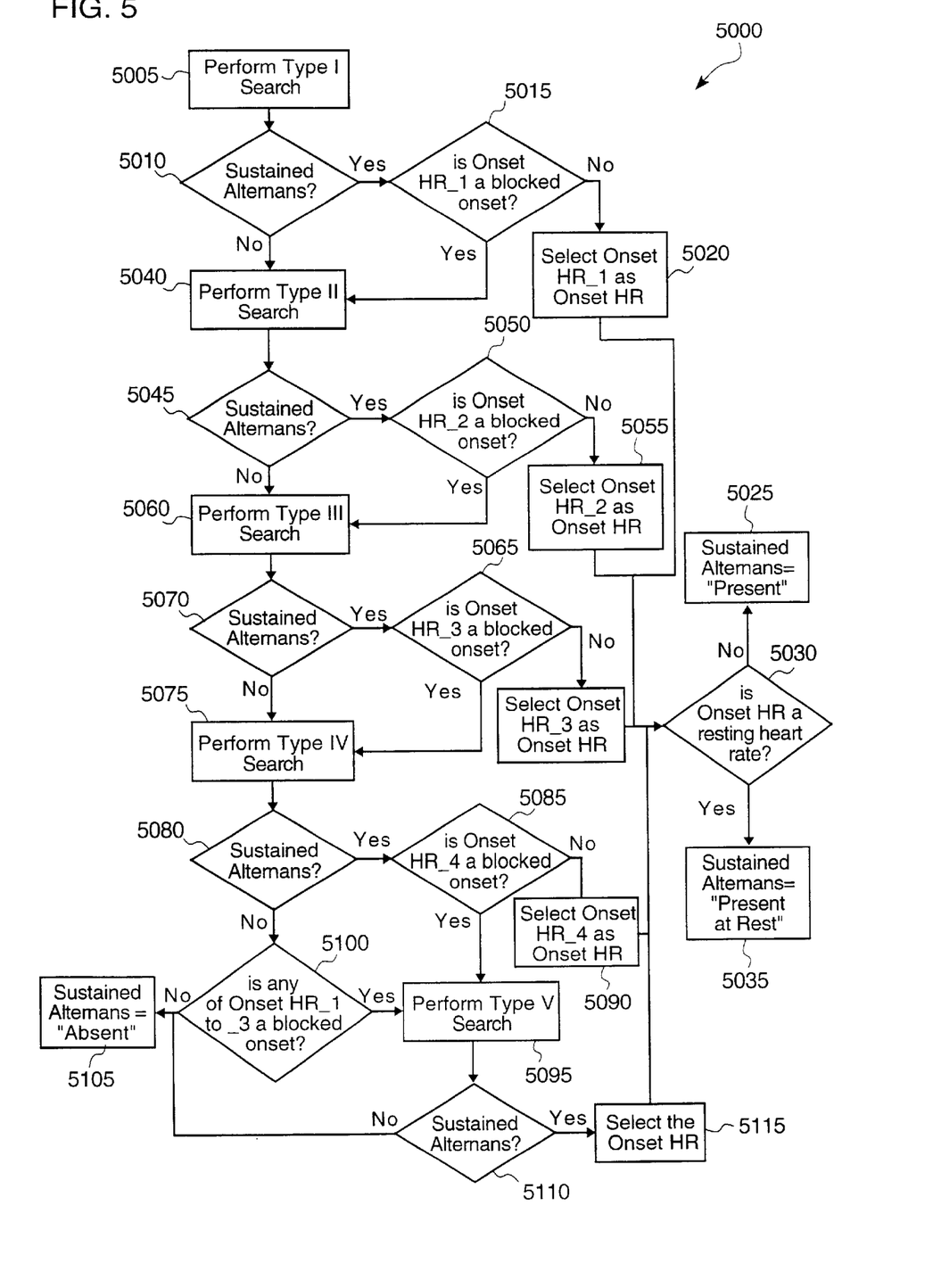
FIG. 5 is a schematic flow diagram illustrating a systematic method for determining the presence of sustained alternans in ECG data.

FIG. 5 illustrates a search method 5000 for determining whether or not sustained alternans exists in heart rate data. The search procedure may include different search algorithms, such as, for example, a basic Onset HR search (Type I), a high heart rate exception search (Type II), a skip recovery search (Type III), a post Max HR search (Type IV), and a reverse Onset HR search (Type V).

The search procedure 5000 begins by performing the Type I search (step 5005). If sustained alternans is determined to exist (step 5010) a further determination is made as to whether an Onset HR__1 determined by the Type I search is a blocked onset (step 5015). An Onset HR is a blocked onset (blocked onset heart rate) when an initial BLOCK__EPOCH__CHECK (e.g., about 7) epochs of heart rate data are examined and the majority of the examined epochs are found to contain bad beats, high noise, or leads-off conditions. If the Onset HR__1 is not a blocked onset, then Onset HR__1 is selected as Onset HR (step 5020) and the search method 5000 returns a determination of "Present" (step 5025) unless the Onset HR is less than a resting heart rate threshold (step 5030). The resting heart threshold is defined as the minimum clean heart rate +/−REST__ALT__THRESH, which, in one implementation, has a value of 2 BPM. If the Onset HR is less than a resting heart rate threshold then the search method 5000 returns a determination of "Present at Rest" (step 5035). If, however, the Onset HR__1 is a blocked onset (step 5015), or if sustained alternans is not determined to exist by the Type I search (step 5010), then a Type II search is performed (step 5040).

If the Type II search (step 5040) determines that sustained alternans exists (step 5045), then a further determination is made as to whether an Onset HR__2 determined by the Type II search is a blocked onset (step 5050). If the Onset HR__2 is not a blocked onset, then Onset HR__2 is selected as the Onset HR (step 5055) and the search method 5000 returns a determination of "Present" (step 5025) unless the Onset HR is less than the resting heart rate threshold (step 5030). If the Onset HR is less than the resting heart rate threshold (step 5030), then the search method 5000 returns a determination of "Present at Rest" (step 5035). If, however, the Onset HR__2 is a blocked onset (step 5050), or if sustained alternans is not determined to exist by the Type II search (step 5045), then a Type III search is performed (step 5060).

The Type III search proceeds in essentially the same manner as the Type II search described above. If the Type III search (step 5060) is determined to have produced a blocked onset (step 5065), Onset HR__3, or if sustained alternans is not determined to exist by the Type III search (step 5070), then a Type IV search is performed (step 5075).

If the Type IV search (step 5075) determines that sustained alternans exists (step 5080), then a further determination is made as to whether an Onset HR__4 determined by the Type IV search is a blocked onset (step 5085). If the Onset HR__4 is not a blocked, onset then Onset HR__4 is selected as the Onset HR (step 5090), and the search procedure returns a determination of "Present" (step 5025) unless the Onset HR is less than the resting heart rate threshold (step 5030). If the Onset HR is less than the resting heart rate threshold (step 5030), then the search procedure returns a determination of "Present at Rest" (step 5035).

If the Type IV search does not determine that sustained alternans exists (step 5080), then the Type V search may be performed (step 5095) if any of Onset HR__1, Onset HR__2, or Onset HR__3, is a blocked onset (step 5100). Otherwise, if none of these is blocked onset (step 5100), then the search method 5000 returns a determination of "Absent" (step 5105). If the Onset HR__4 determined by the Type IV search is a blocked onset, then a Type V search is performed (step 5100).

If the Type V search (step 5100) does not determine that sustained alternans exists (step 5110), then the search method 5000 returns a determination of "Absent" (step 5105). If, however, sustained alternans are determined to exist by the Type V Search (step 5110), then the search method 5000 selects between one or more blocked Onset HR values and Onset HR__5 (step 5115). For example, Onset HR__5 may be selected as the Onset HR if Onset HR__5 is less than or equal to the lowest blocked onset heart rate minus OFF__BLOCK__THRESH, a value of about 5 BPM. Otherwise, the lowest blocked onset heart rate may be selected as the Onset HR. The search method 5000 returns a determination of "Present" (step 5025) unless the Onset HR is less than the resting heart rate threshold (step 5030). If the Onset HR is less than the resting heart rate threshold (step 5030), then the search procedure returns a determination of "Present at Rest" (step 5035).

The search algorithms used by the search method 5000 (e.g., search Types I-V of steps 5005, 5040, 5060, 5075, and 5095) are generally similar. For ease of description, the Type I search is discussed in detail and descriptions of redundant aspects of the search Types II–V are omitted for brevity.

The Type I search may, in general, be performed sequentially for each signal (e.g., VM-VZ, V1-V6), with a finding of sustained alternans in any one signal resulting in a determination that sustained alternans exists. The Type I search also may process a signal by partitioning the signal into sequential epochs of data, where an epoch may be defined as a set of 128 consecutive heart beats in an ECG signal.

The Type I search is based on the understanding that the occurrence of T-wave alternans is heart rate dependent. T-wave alternans may appear above a threshold heart rate and last until the heart rate drops below the threshold. The threshold is patient specific and is normally in the range of about 80–110 BPM. Nevertheless, other threshold heart rate ranges may be more appropriate depending on the patient population and the physician's understanding of the subject patient.

The Type I search identifies the lowest heart rate, which is called the Onset HR, at which T-wave alternans occurs for greater than half of the time period for which the heart rate of the patient is above or equal to the Onset HR. Nevertheless, dips in the heart rate of the patient of up to HR__DIP__ALLOW, a value of about 10 BPM, are allowed in order to prevent slight heart rate dips from disqualifying otherwise sustained alternans.

Additional conditions must be satisfied with respect to the epochs of heart rate data that occur subsequent to the epoch associated with the Onset HR. First, the normalized alternans fraction, defined as the ratio of total alternans area (described hereafter) to the product of the V_ALT_THRESHOLD, a value of about 1.9 V, and total segment duration, must be at least equal to ALT_FRAC_THRESH, a value of about 0.68. Second, there must be there must exist at least one continuous minute of heart rate data above the Onset HR during which alternans exists for at least MIN_SUST_ALT_DUR1, a value of about 50 seconds. Third, the first epoch with a heart rate greater than or equal to Onset HR should exhibit alternans. Fourth, gaps in the alternans that are greater than MAX_GAP, a value of about 15 seconds, should satisfy one of the following criteria: the gap must be shorter than the preceding interval of alternans; or the gap must be shorter than the product of the cumulative sum of all preceding alternans interval lengths and CUMUL_COEFF, where CUMUL_COEFF is typically a value of about 0.75. Fifth, the first epoch with a heart rate greater than or equal to Onset HR should have alternans. Finally, there should be at least one epoch containing alternans that is free of artifacts for patient heart rates greater than or equal to the Onset HR.

The total alternans area, used to determine the normalized alternans fraction above, may be calculated as the inner/dot product of an associated clipped alternans level and the duration of the alternans segments. In one implementation, the clipped alternans level is determined as follows. First, the clipped alternans level is set to 2.2 $\mu V$ if the alternans level is greater than 2.2 $\mu V$. Second, when the alternans level is less than or equal to 2.2 $\mu V$ and is greater than or equal to 1.2 $\mu V$, then the clipped alternans level is set to the alternans level. Third, if the alternans level is less than 1.2 $\mu V$, then the clipped alternans level is set to zero. Finally, if the alternans K-score is less than 3, the clipped alternans level is set to zero. The alternans K-Score is the ratio of the alternans level to the standard deviation of the alternans noise.

The Type I search reports that there are sustained alternans when sustained alternans are detected and the listed conditions are satisfied. Otherwise, the Type I search reports that there are no sustained alternans.

The Type II search is based on the understanding that, in certain situations, the T-wave alternans decreases or disappears at high heart rates. Under these circumstances, the Type I search might not find T-wave alternans at all heart rates above the Onset HR. Therefore, the Type II search ignores time periods for which the heart rate is above a certain disease dependent rate.

The Type II search is essentially similar to the Type I search with the addition of two more conditions. The first condition is that alternans should exist during at least MIN_ALT_PER of the time the smoothed heart rate is equal to or above the Onset HR, and should exist during the time that the smoothed heart rate is less than MAX_HR_LIMIT, a disease dependent value that typically is about 120 BPM. The second condition is that at least about two continuous minutes of the heart rate data must exhibit alternans for at least MIN_SUST_ALT_DUR2, a value of about 110 seconds. The Type II search reports that sustained alternans exist when sustained alternans are detected and the listed conditions are satisfied. Otherwise, the Type II search reports that sustained alternans do not exist.

The Type III search is based on the understanding that patients exhibit highly varying heart rate profiles during recovery. In many cases, the heart rate decreases very rapidly and masks the measurement of T-wave alternans. Therefore, this search avoids using the recovery time data. Again, the Type III search is essentially similar to the Type I search. It is different in that all segments after the exercise stage are ignored. The Max HR is calculated based upon the truncated heart rate data set.

The Type IV search is designed to detect sustained alternans in situations where the heart rate of the patient peaks before the end of the exercise period. The Type IV search first verifies that there is a total alternans duration of at least about 2 minutes. If so, then the Type IV search verifies that there is also at least one continuous interval of alternans of a duration of at least MIN_SUST_ALT_DUR5, a patient population dependent value that typically is about 110 seconds. The Type IV search is performed once including all of the epochs of heart rate data and then again but excluding the epochs of heart rate data with noise, bad beats, or leads-off. The Type IV search drops the condition that alternans occurs for most of the time period for which the patient heart rate is above the Onset HR.

The Type V search is designed to search heart rate data where the appearance/measurement of T-wave alternans is delayed because of occurrences of bad beats and high noise. The bad beats and high noise can complicate the accurate measurement of the Onset HR that is crucial to the correct determination of sustained alternans. Hence, the Type V search reverses the heart rate data timeline and the Onset HR is determined from the recovery end of the heart rate data. The Type V search is performed only if the Onset HR determined in searches Type 1-4 has been labeled a blocked onset.

Figure 6:
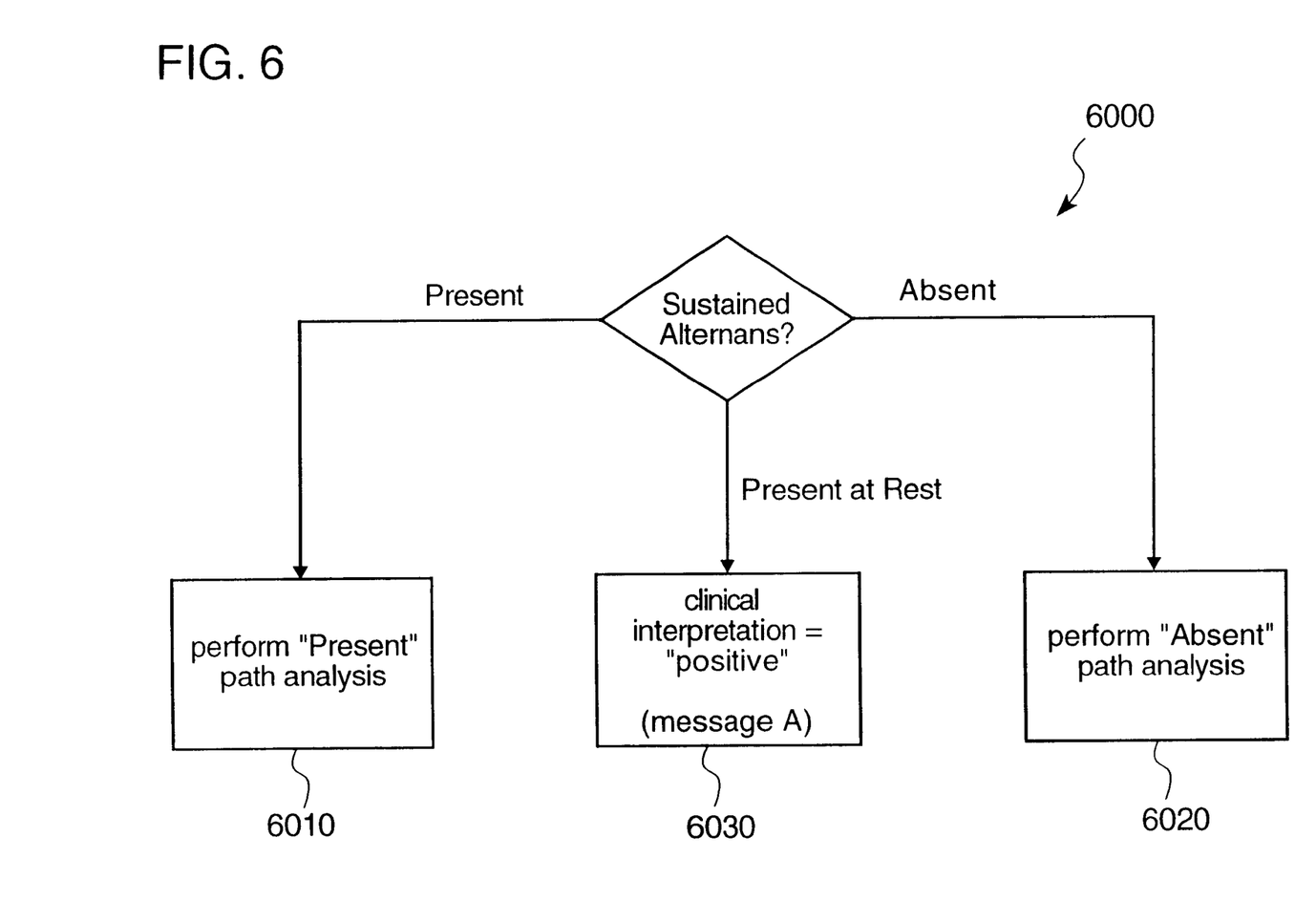
FIG. 6 is a schematic flow diagram illustrating a systematic method for making a clinical interpretation based on alternans results.

FIG. 6 illustrates a method 6000 that may be used by the interpretation system 1040 to derive a clinical interpretation 1045 associated with the alternans results 1015. The method 6000 provides a decision tree that the interpretation system 1040 may apply to the interpretation parameters 1035 to determine a clinical interpretation 1045 of "positive", "negative", or "indeterminate." As described above, the interpretation parameter sustained alternans 1065 may take a value of "Present," "Absent," or "Present at Rest." When sustained alternans 1065 is "Present," the "Present" path analysis 6010 is performed, and when sustained alternans 1065 is "Absent," the "Absent" path analysis 6020 is performed. When sustained alternans 1065 is "Present at Rest," a clinical interpretation 1045 of "Positive" is returned (step 6030).

Figure 7:
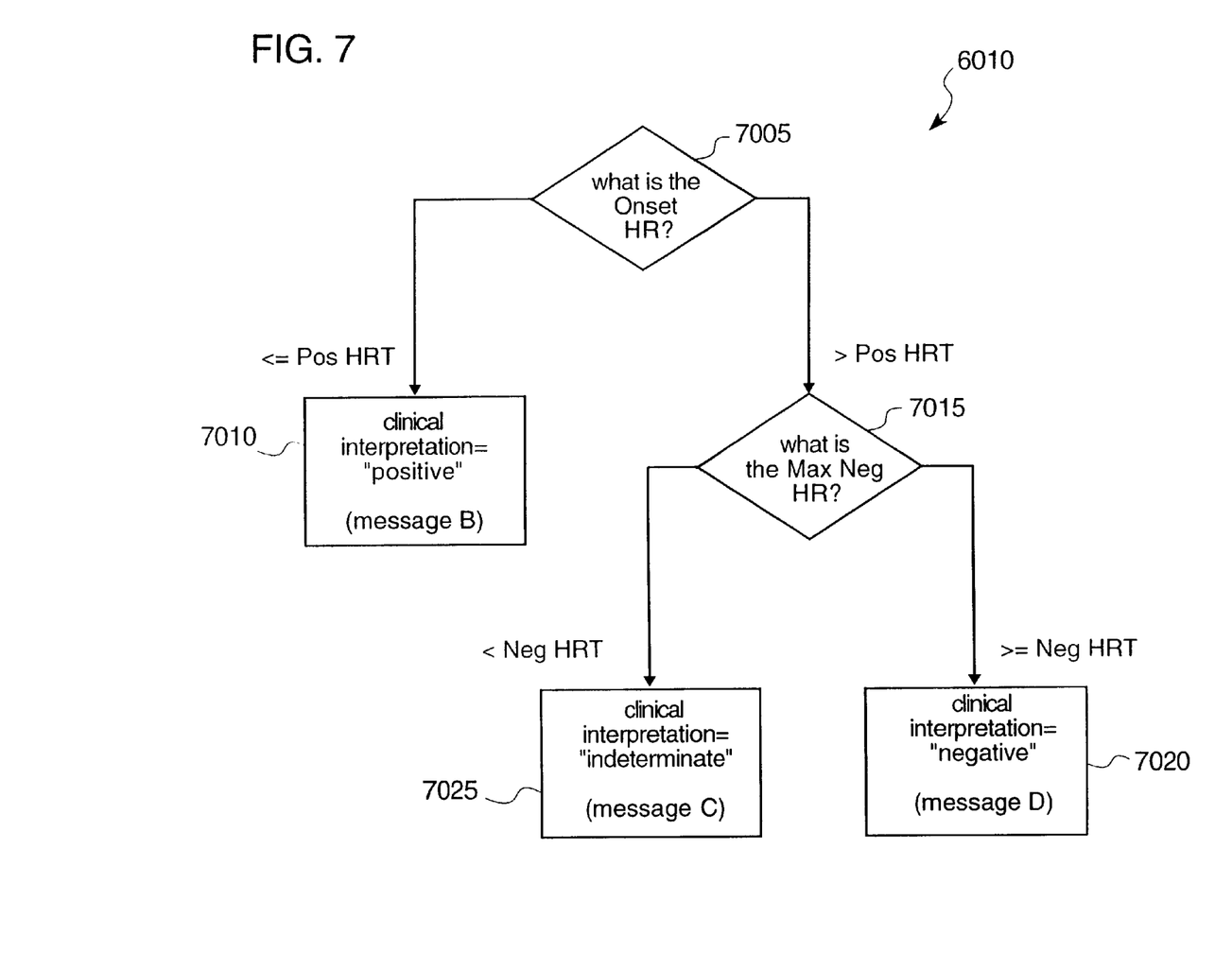
FIG. 7 is a schematic flow diagram illustrating a method for making a clinical interpretation based on alternans results that indicate that sustained alternans is present and that may be used in implementing the method of FIG. 6.

FIG. 7 illustrates an analysis flow 6010 suitable for use as the "Present" path analysis flow of the method 6000 of FIG. 6. When sustained alternans 1065 is "Present" and the Onset HR is at or below a first threshold (Pos HRT) (step 7005), such as, for example, about 110 beats-per-minute (BPM), then an automatic clinical interpretation of "positive" is produced (step 7010). If the Onset HR is above Pos HRT (step 7005) and the Max Neg. HR is greater than or equal to a second threshold (Neg HRT) (step 7015), such as, for example, about 105 BPM, then an automatic clinical interpretation of "negative" is produced (step 7020). If Max Neg. HR is less than Neg HRT (step 7015), an automatic clinical interpretation of "indeterminate" is produced (step 7025).

Figure 8:
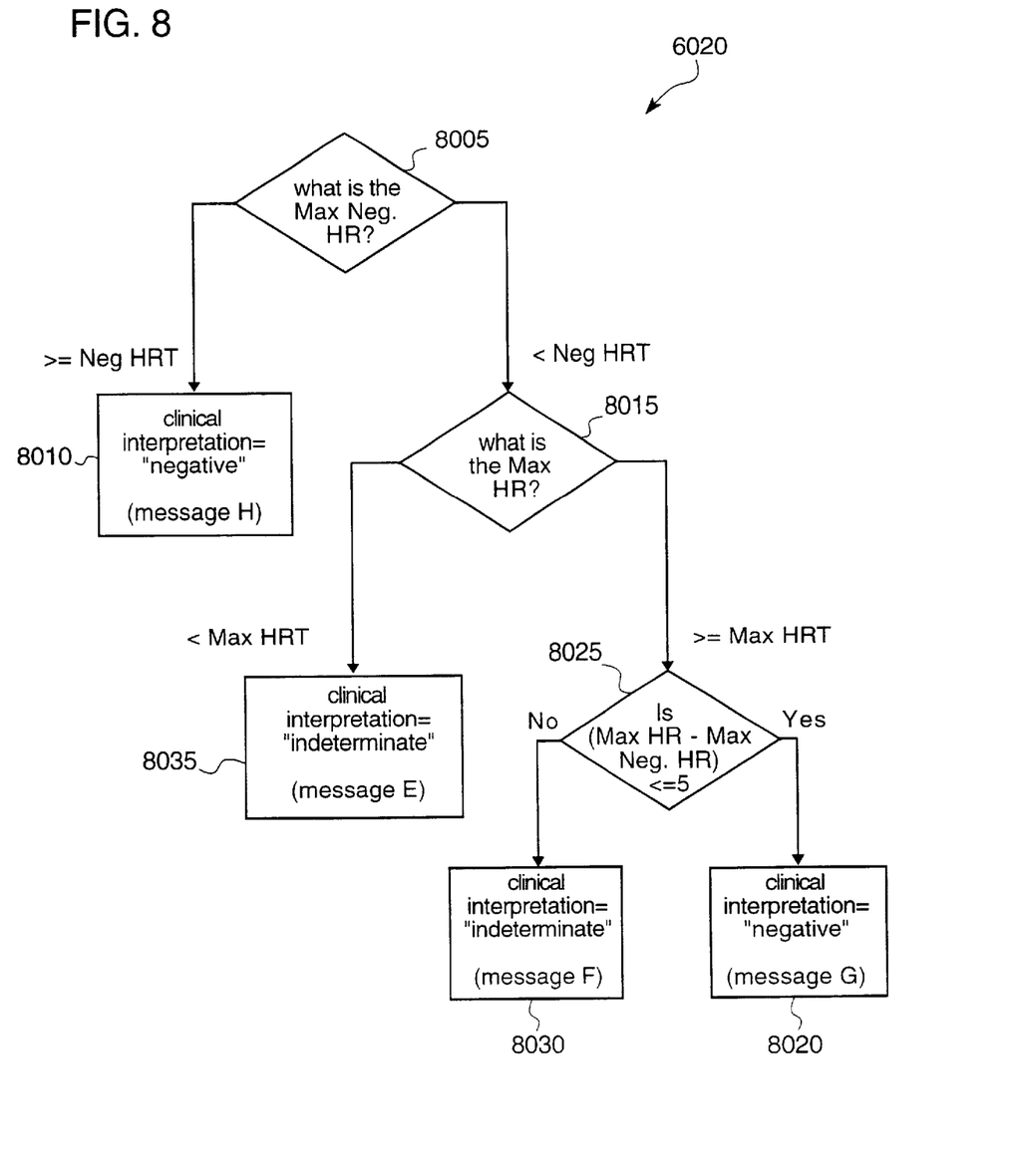
FIG. 8 is a schematic flow diagram illustrating a method for making a clinical interpretation based on alternans results that indicate that sustained alternans is absent and that may be used in implementing the method of FIG. 6.

FIG. 8 illustrates an analysis flow 6020 suitable for use as the "Absent" path analysis flow of the method 6000 of FIG. 6. When Sustained Alternans is "Absent," if Max Neg. HR is greater than or equal to Neg HRT (step 8005), then an automatic clinical interpretation of "negative" is produced (step 8010). However, where Max Neg. HR is less than Neg HRT (step 8005), and Max HR is greater than or equal to a third threshold (Max HRT) (step 8015), such as, for example, about 110 BPM, then an automatic clinical interpretation of "negative" is produced (step 8020) if Max HR minus Max Neg. HR is less than or equal to about 5 BPM (step 8025). If Max HR minus Max Neg. HR is greater than about 5 BPM (8025), then an automatic clinical interpretation of "indeterminate" is produced (step 8030). Moreover, where Max Neg. HR is less than Neg. HRT (step 8005), and Max HR also is less than Max HRT (step 8015), then an automatic clinical interpretation of "indeterminate" is produced (step 8035).

Finally, the system presents the interpretation results 1025. The interpretation results 1025 may include a visual representation of the alternans measures 1005 along with the reference signals 1010, the automatic clinical interpretation 1045, and an explanation of a diagnostic process followed to arrive at the automatic clinical interpretation 1045. The interpretation results 1025 may be presented in a way that permits a physician to efficiently review the interpretation results 1025 and to decide to either accept or override the automatic clinical interpretation 1045 as appropriate.

Figure 9:
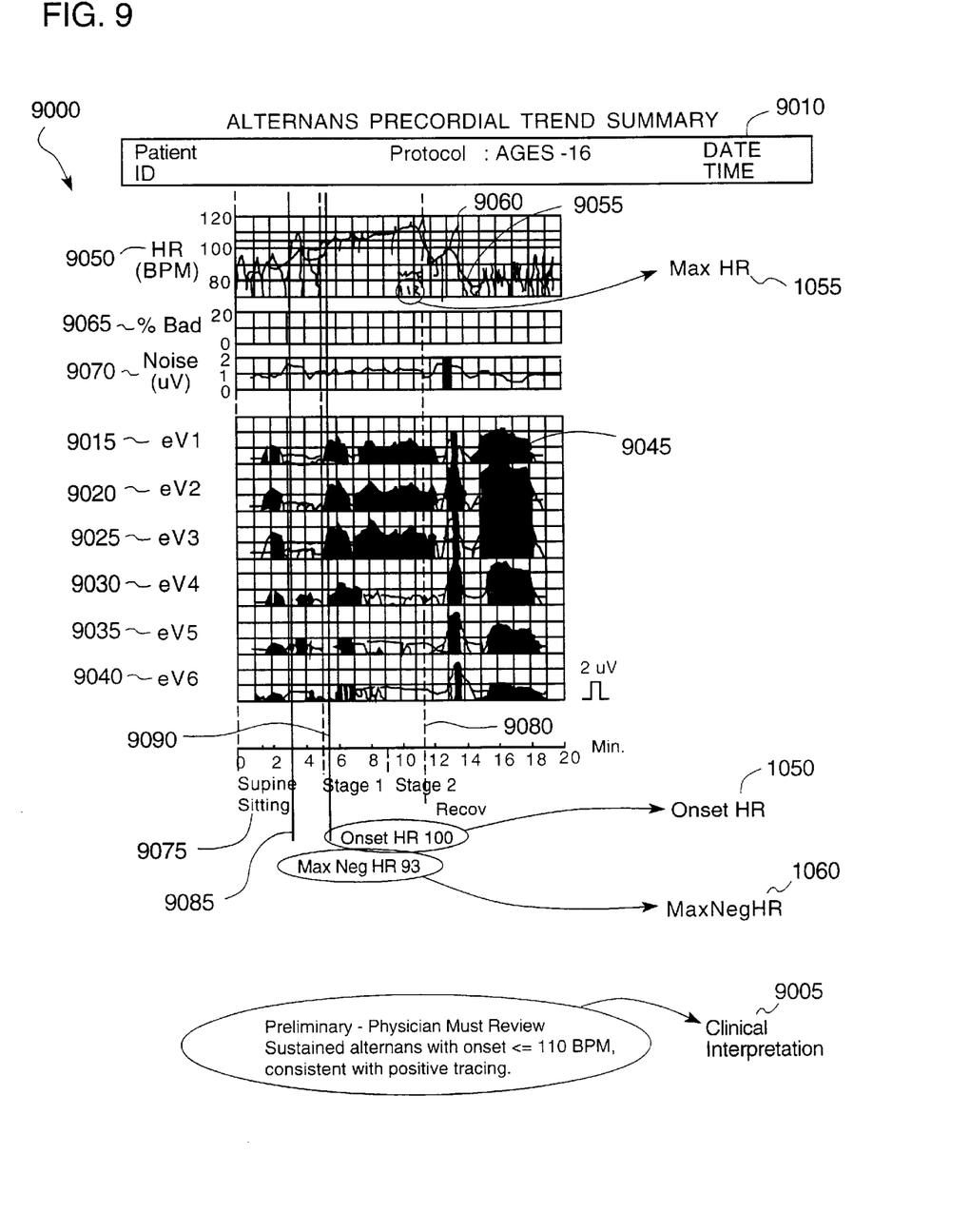
FIG. 9 illustrates a sample T-wave alternans trend report including clinical interpretation results produced by the system of FIG. 1.

FIG. 9 illustrates an alternans trend report 9000 produced by the system 1000. In one implementation, the interpretation results 1025 of the automated system 1000 are annotated on report 9000, as shown in FIG. 9. In this implementation, the trend report 9000 displays the Onset HR 1050, Max Neg. HR 1060, and the Max HR 1055, along with a message 9005 describing the clinical interpretation.

Figure 10:
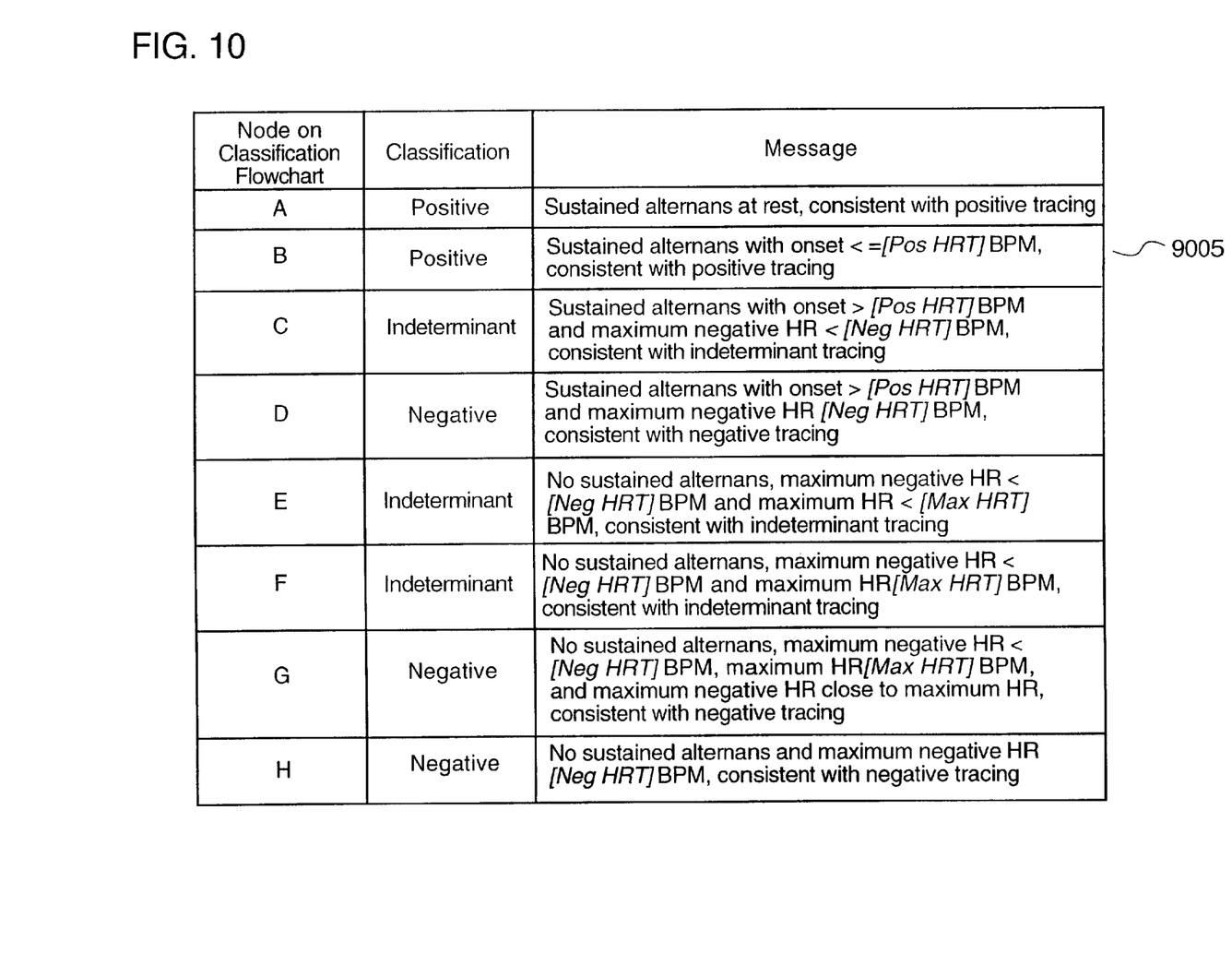
FIG. 10 is a table containing illustrative clinical interpretation messages that correspond to each terminal node of the decision tree represented in FIGS. 7–8.

Referring to FIG. 10, a unique interpretation message may be printed that corresponds to a terminal node in the decision trees of FIGS. 6–8. The various terminal nodes of FIGS. 6–8 are labeled to correspond to messages A through H of FIG. 10. For example, a terminal node of FIG. 7 is labeled to correspond to message B of FIG. 10, and also is the clinical interpretation message 9005 represented by report 9000.

Report 9000 may be displayed on a monitor (not shown) or produced in printed form by a printer (not shown). Report 9000 also may be produced in other ways. For example, report 9000 may be produced as an electronic file that is accessible at a later time to permit visual inspection of the alternans measurements relative to the reference signals at that time.

The report 9000 includes an informational segment 9010. This segment identifies the title of the report ("Alternans Precordial Trend Summary"), the patient (by name and identification number), the testing/exercise protocol that resulted in the alternans measurements, and the date and time at which the measurements were produced.

Report 9000 may include alternans measurements for the V1-V6 leads. These measurements are identified as eV1 (9015), eV2 (9020), eV3 (9025), eV4 (9030), eV5 (9035), and eV6 (9040).

Alternans measurements for the vector leads (e.g., eVM, eX, eY and eZ) (not shown) also may be presented. The "e" preceding the name of each signal indicates that the signal has been enhanced using the noise reduction techniques noted above. The alternans measurements are displayed with respect to a grid having vertical sections that each correspond to 2 microvolts of alternans and horizontal sections that each correspond to a period of one minute. Time segments for which the alternans ratio is greater than or equal to a threshold value are indicated by dark gray shading 9045. In report 9000, the threshold equals three.

Time segments for which values of the reference signals are within ranges that have been determined to be acceptable may be indicated by a black line (not shown) along the horizontal axis. The black line may indicate that the time segments are free of artifacts that would prevent the alternans measures corresponding to the time segments from being representative of actual alternans.

Report 9000 also includes a number of reference signals. Starting at the top of the report, the first reference signal is the heart rate 9050 in beats per minute (BPM). Measures of both the mean heart rate 9055 and the instantaneous heart rate 9060 are provided. It is known that alternans may be detected more easily when the heart rate is elevated. Accordingly, inclusion of the heart rate permits an operator to determine whether high levels of alternans have occurred in periods in which they would be expected.

Next, report 9000 includes a measure 9065 of the percentage of bad beats (i.e., beats that are more than 10% premature or beats having shapes that differ from the shape of a normal beat by more than 10%). Periods for which more than a predetermined percentage of the beats are bad are indicated by light gray shading. In report 9000, the predetermined percentage is 10%. Black lines are not displayed along the horizontal axes of the alternans measurements for periods in which the percentage of bad beats exceeds the predetermined percentage.

Report 9000 next includes a measure 9070 of vector magnitude noise as measured, for example, in the eVM lead (the eVM signal is not displayed in the Report 9000). Noise levels above a threshold level are indicated by light gray shading. High noise may obscure alternans and results in a false negative determination.

The noise measure 9070 is followed by the alternans measurements 9015-9040. After the alternans measurements, report 9000 identifies stages of the protocol for which the alternans measurements are generated. The stages are identified by labels 9075 and corresponding dashed vertical lines 9080. The protocol illustrated in report 9000 begins with the patient in a supine position, as indicated by the label "Supine." After five minutes, the patient begins physical exertion, indicated by the state "1" label. At about nine minutes into the protocol, the patient's level of exercise increases. This is indicated by the stage "2" label. Finally, at about eleven minutes and 30 seconds into the protocol, the patient begins a recovery period. This is indicated by the "recovery" label.

Report 9000 also includes information corresponding to segments (i.e., a group of 128 beats) automatically identified by the system 1000 as satisfying a set of selection requirements, such as, for example, selection by the system operator of the segment, and/or determination by the system 1000 that the segment is associated with a designated parameter (e.g., MaxNegHR). Two segments are illustrated in report 9000. The first, indicated by a vertical line 9085, indicates an association with MaxNegHR and, in report 9000, occurs at about 3 minutes and 10 seconds into the protocol. The second segment is indicated by a vertical line 9090 and indicates an association with Onset HR. In report 9000, the second segment occurs at about 5 minutes and twenty-five seconds into the protocol.

To obtain additional information regarding a segment the system may allow the system operator to select a segment. The system then may, for example, provide additional data at the upper left corner of each alternans measurement (not shown). The additional data may include, for example, numbers that correspond, respectively, to the alternans voltage, the alternans ratio, and the alternans noise level for the selected segment.

Report 9000 also may include the rate of exercise (not shown). When a bicycle is used to perform exercise, the rate of exercise may be displayed in rotations per minute relative to the heart rate. Repetitive movement at one half of the heart rate can result in a peak in the signal power spectrum that may mimic alternans. Accordingly, an exercise rate that differs from ⅓ or ⅔ of the heart rate by 7% (i.e., does not fall in the ranges from 26% to 40% or from 60% to 74% of the heart rate) for 8% or more of the beats in any group of 128 beats (and does not equal zero) may be shaded in light gray. Black lines will not be displayed along the horizontal axes of the alternans measurements for periods in which the exercise measure is shaded gray.

Also, report 9000 may display a measure of respiration (not shown). The respiration measure may indicate the presence and amplitude of a peak in the respiration waveform at 0.25 cycles per beat. The respiration measure may be expressed using the power spectrum analysis or time domain analysis methods as discussed above. Periods for which the amplitude of the peak exceeds a threshold value may be indicated by light gray shading. Black lines will not be displayed along the horizontal axes of the alternans measurements for periods in which the respiration measure is shaded gray.

Report 9000 also may include a reference signal referred to as HR Delta (not shown). HR Delta may correspond to the difference between the highest and lowest instantaneous heart rates in a 128 beat interval. Rapidly varying heart rates can result in false alternans measurements. Accordingly, the HR Delta measure may be shaded gray for periods in which HR Delta exceeds a threshold level. Black lines will not be displayed along the horizontal axes of the alternans measurements for periods in which HR Delta is shaded gray.

Other measures of heart rate variability also may be used. For example, it has been found that a low frequency fluctuation in the heart rate tends to break up a pattern of alternans and increase the difficulty of detecting alternans.

Other embodiments are within the scope of the following claims.

What is claimed is:

1. A method of interpreting alternans data comprising:
   accessing alternans data;
   automatically evaluating the alternans data to produce one or more interpretation parameters based on the alternans data;
   using the interpretation parameter to generate interpretation results related to the alternans data; and
   making the interpretation results accessible for examination.

2. The method of claim 1 wherein accessing alternans data comprises receiving the alternans data from an electrocardiogram system.

3. The method of claim 1 wherein accessing alternans data comprises reading stored alternans data from a storage medium.

4. The method of claim 1 wherein accessing alternans data comprises calculating the alternans data from electrocardiogram data.

5. The method of claim 1 wherein the alternans data comprise alternans measures.

6. The method of claim 5 wherein the alternans data further comprise a reference signal associated with a factor that may affect the quality of the alternans measures.

7. The method of claim 6 wherein the reference signal masks the presence of alternans.

8. The method of claim 6 wherein the reference signal mimics the presence of alternans.

9. The method of claim 6 wherein the reference signal includes a measure of noise in the alternans data.

10. The method of claim 5 wherein the alternans data further comprise a reference signal associated with a factor that may affect generation of alternans.

11. The method of claim 10 wherein the reference signal includes a measure of the patient's heart rate.

12. The method of claim 10 wherein the reference signal includes a measure of the patient's respiratory activity.

13. The method of claim 1 wherein the interpretation parameters comprise a measure of a highest heart rate in the alternans data.

14. The method of claim 1 wherein the interpretation parameters comprise a measure of a highest heart rate at which sustained alternans is definitely not present.

15. The method of claim 1 wherein the interpretation parameters comprise a measure of a heart rate above which sustained alternans exists and below which sustained alternans does not exist.

16. The method of claim 1 wherein the interpretation parameters comprise an indication of the existence or non-existence of sustained alternans.

17. The method of claim 1 wherein automatically evaluating the alternans data comprises automatically evaluating a measure of alternans indicative of the presence of sustained alternans.

18. The method of claim 17 wherein the measure of the alternans comprises a measure of a voltage associated with the alternans.

19. The method of claim 17 wherein the measure of the alternans comprises a measure of an area associated with the alternans.

20. The method of claim 17 wherein the measure of the alternans comprises a measure of noise associated with the alternans.

21. The method of claim 20 wherein the measure of the noise associated with the alternans comprises a measure of a standard deviation of the noise.

22. The method of claim 17 wherein the measure of the alternans comprises a measure of a temporal duration of the alternans.

23. The method of claim 17 wherein the measure of the alternans comprises a measure of a power spectrum of the alternans.

24. The method of claim 17 wherein the measure of the alternans comprises a dynamic estimation of a magnitude related to the alternans.

25. The method of claim 24 wherein the dynamic estimation comprises a complex demodulation.

26. The method of claim 17 wherein the measure of the alternans comprises a measure of gaps in the alternans.

27. The method of claim 17 wherein the measure of the alternans comprises a measure of the alternans based upon evaluation of time reversed alternans data.

28. The method of claim 1 wherein automatically evaluating the alternans data comprises automatically using a first search to search the alternans data for sustained alternans.

29. The method of claim 28 further comprising automatically using a different search to search the alternans data for sustained alternans after using the first search to search the alternans data for sustained alternans.

30. The method of claim 29 wherein the different search is used to search the alternans data for sustained alternans after the first search does not find sustained alternans in the alternans data.

31. The method of claim 29 wherein the different search is used to search the alternans data for the sustained alternans after a determination is made that the findings of the first search are suspect as a result of a poor quality of the alternans data.

32. The method of claim 1 wherein automatically evaluating the alternans data comprises evaluating the alternans data provided by an individual electrocardiogram lead.

33. The method of claim 1 wherein automatically evaluating the alternans data comprises evaluating a combination of adjacent precordial electrocardiogram leads.

34. The method of claim 1 wherein the interpretation results include the interpretation parameter.

35. The method of claim 1 wherein the interpretation results include a clinical interpretation regarding the existence of sustained alternans in the alternans data.

36. The method of claim 35 wherein the clinical interpretation is either positive, negative, or indeterminate.

37. The method of claim 1 wherein using the interpretation parameter comprises using the interpretation parameter to traverse a decision tree to produce the interpretation results based on the alternans data.

38. The method of claim 1 wherein using the interpretation parameter comprises comparing the interpretation parameter to a heart rate threshold to produce the interpretation results based on the alternans data.

39. The method of claim 1 wherein making the interpretation results accessible comprises graphically displaying the alternans measure, the reference signal, and the interpretation results.

40. The method of claim 39 wherein graphically displaying further comprises displaying the alternans measure and the reference signal using a common time axis.

41. The method of claim 40 wherein graphically displaying further comprises graphically associating the interpretation results to an associated feature of the alternans measure and/or the reference signal.

42. The method of claim 41 wherein graphically displaying further comprises providing a message describing the interpretation results.

43. The method of claim 1 wherein making the interpretation results accessible comprises storing the alternans measure, the reference signal, and/or the interpretation results in a human or machine readable format.

44. A system for interpreting alternans data comprising:
accessing means for accessing alternans data;
evaluation means for automatically evaluating the alternans data and producing one or more interpretation parameters based on the alternans data;
generation means for generating interpretation results related to the alternans data using the interpretation parameter; and
output means for making the interpretation results accessible for examination.

45. The system of claim 44 wherein the accessing means comprises a receiving means for receiving the alternans data from an electrocardiogram system.

46. The system of claim 44 wherein the alternans data comprise alternans measures.

47. The system of claim 46 wherein the alternans data further comprise a reference signal associated with a factor that may affect the quality or generation of the alternans measures.

48. The system of claim 44 wherein the evaluation means comprises a first search means to automatically search the alternans data for sustained alternans.

49. The system of claim 48 further comprising a different search means to automatically search the alternans data for sustained alternans after the first search means has searched the alternans data for sustained alternans.

50. The system of claim 49 wherein the different search means searches the alternans data for sustained alternans after the first search means does not find sustained alternans in the alternans data.

51. The system of claim 49 wherein the different search means searches the alternans data for the sustained alternans after a determination means determines that the findings of the search of the first search means are suspect as a result of a poor quality of the alternans data.

52. The system of claim 44 wherein using the interpretation parameter comprises using the interpretation parameter to traverse a decision tree to produce the interpretation results based on the alternans data.

53. The system of claim 44 wherein the output means makes the interpretation results accessible by graphically displaying the alternans measure, the reference signal, and the interpretation results.

54. The system of claim 53 wherein graphically displaying further comprises graphically associating the interpretation results to an associated feature of the alternans measure and/or the reference signal.

55. The system of claim 54 wherein graphically displaying further comprises providing a message describing the interpretation results.

56. A computer program stored on a computer readable medium or a propagated signal for interpreting alternans data, the computer program comprising:
an accessing code segment that causes a computer to access alternans data;
an evaluation code segment that causes the computer to automatically evaluate the alternans data and produce one or more interpretation parameters based on the alternans data;
a generation code segment that causes the computer to generate interpretation results related to the alternans data using the interpretation parameter; and
an output code segment that causes the computer to make the interpretation results accessible for examination.

57. The computer program of claim 56 wherein the accessing code segment comprises a receiving code segment that causes the computer to receive the alternans data from an electrocardiogram system.

58. The computer program of claim 56 wherein the alternans data comprise alternans measures.

59. The computer program of claim 58 wherein the alternans data further comprise a reference signal associated with a factor that may affect the quality or generation of the alternans measures.

60. The computer program of claim 56 wherein the evaluation code segment comprises a first search code segment that caused the computer to automatically search the alternans data for sustained alternans.

61. The computer program of claim 60 further comprising a different search code segment that causes the computer to automatically search the alternans data for sustained alternans after the first search code segment has caused the computer to search the alternans data for sustained alternans.

62. The computer program of claim 61 wherein the different search code segment causes the computer to search the alternans data for sustained alternans after the computer under the control of the first search code segment does not find sustained alternans in the alternans data.

63. The computer program of claim 61 wherein the different search code segment causes the computer to search the alternans data for the sustained alternans after a determination code segment causes the computer to determine that the search findings of computer made under the control of the first search code segment are suspect as a result of a poor quality of the alternans data.

64. The computer program of claim 56 wherein using the interpretation parameter comprises using the interpretation parameter to traverse a decision tree to produce the interpretation results based on the alternans data.

65. The computer program of claim 56 wherein the output code segment causes the computer to make the interpretation results accessible by graphically displaying the alternans measure, the reference signal, and the interpretation results.

66. The computer program of claim 65 wherein graphically displaying further comprises graphically associating the interpretation results to an associated feature of the alternans measure and/or the reference signal.

67. The computer program of claim 66 wherein graphically displaying further comprises providing a message describing the interpretation results.

* * * * *